US010822665B2

(12) United States Patent
Bezenger et al.

(10) Patent No.: US 10,822,665 B2
(45) Date of Patent: Nov. 3, 2020

(54) METHOD FOR MAKING CHEESE

(75) Inventors: Marie-Claude Bezenger, Bruyeres-le-chatel (FR); Ilka Eppert, Miege (CH); Niels Kristian Soerensen, Birkeroed (DK); Erik Hoeier, Valby (DK); Anne-Gaelle Le Tual, Saint Felix de Lodez (FR); Mikkel Laust Broe, Middelfart (DK); Fergal P. Rattray, Valby (DK)

(73) Assignee: CHR. HANSEN A/S, Hoersholm (DK)

( * ) Notice: Subject to any disclaimer, the term of this patent is extended or adjusted under 35 U.S.C. 154(b) by 920 days.

(21) Appl. No.: 12/596,961

(22) PCT Filed: Apr. 17, 2008

(86) PCT No.: PCT/EP2008/054664
§ 371 (c)(1),
(2), (4) Date: Mar. 3, 2010

(87) PCT Pub. No.: WO2008/128959
PCT Pub. Date: Oct. 30, 2008

(65) Prior Publication Data
US 2010/0178387 A1 Jul. 15, 2010

(30) Foreign Application Priority Data
Apr. 23, 2007 (DK) .................... 2007 00595

(51) Int. Cl.
*A23C 19/032* (2006.01)
*C12R 1/225* (2006.01)
*A23C 19/072* (2006.01)
*A23C 19/05* (2006.01)
*A23C 19/068* (2006.01)

(52) U.S. Cl.
CPC .......... *C12R 1/225* (2013.01); *A23C 19/0323* (2013.01); *A23C 19/05* (2013.01); *A23C 19/0688* (2013.01); *A23C 19/072* (2013.01); *A23Y 2220/29* (2013.01)

(58) Field of Classification Search
CPC . A23C 19/032; A23C 19/0323; A23C 19/072; A23Y 2220/29
USPC ........................................... 426/42
See application file for complete search history.

(56) References Cited

U.S. PATENT DOCUMENTS

2003/0008056 A1*  1/2003  Henry et al. ............. 426/582

FOREIGN PATENT DOCUMENTS

EP  0 633 316 A1  6/1994

OTHER PUBLICATIONS

Germond, J., Lapierre, L., Delley, M., Mollet, B., Felis, G. E., Dellagloi, F., "Evolution of the Bacterial Species Lactobacillus delbrueckii: A Partial Genomic Study with Reflections on Prokaryotic Species Concept," Mol. Biol. Evol., 20(1):93-104 (2003).*
Drake, M. A., Boylston, T. D., Spence, K. D. and Swanson, B. G., "Chemical and sensory effects of a Lactobacillus adjunct in Cheddar cheese," Food Research International, 29:381-387 (1996).*
Excerpt with date highlighted of Awad, S., Ahmed, N., El Soda, M., "Evaluation of isolated starter lactic acid bacteria in Ras cheese ripening and flavor development," Food Chemistry, 103 (2007) 1192-1199, available online as of Feb. 4, 2007, at http://www.sciencedirect.com/science/article/pii/S0308814607001240.*
Peterson, S. D., and Marshall, R. T., "Nonstarter Lactobacilli in Cheddar Cheese: A Review", J. Dairy Sci. 73:1395-1410 (1990).*
E. Tsakalidou et al., "Cell-Wall-Bound Proteinase of *Lactobacillus delbrueckii* subsp. *lactis* ACA-DC 178: Characterization and Specificity for β-Casein," 65 Applied & Environmental Microbiology 2035-40 (1999). Downloaded from http://aem.asm.org/.*
E. Tsakalidou et al., "Cell-Wall-Bound Proteinase of *Lactobacillus delbrueckii* subsp. *lactis* ACA-DC 178: Characterization and Specificity for β-Casein" Applied and Environmental Microbiology, May 1999, vol. 65 No. 5, pp. 2035-2040.
E. Parente et al., "A multiple strain starter for water-buffalo Mozzarella cheese manufacture", LAIT, 1989, vol. 69, pp. 271-279.
M. Fernada Fernandez et al., "A Washed-Curd Goat's Cheese as a Vehicle for Delivery of a Potential Probiotic Bacterium: *Lactobacillus delbrueckii* subsp. *lactis* UO 004", Journal of Food Protection, vol. 68, No. 12, 2005, pp. 2665-2671.
Sameh Awad et al., "Evaluation of isolated starter lactic acid bacteria in Ras cheese ripening and flavour development", Food Chemistry 104 (2007) 1192-1199.
Fergal P. Rattray et al., "Specificity of an Extracellular Proteinase from *Brevibacterium linens* ATCC 9174 on Bovine $\alpha_{s1}$-Casein", Applied and Environmental Microbiology, Feb. 1996, vol. 62, No. 2, pp. 501-506.
M. El Soda et al., "Adjunct Cultures: Recent Developments and Potential Significance to the Cheese Industry", Marschall Rhodia International Dairy Science and Award Lecture, J. Dairy Science 2000, 83: 609-619.
C.M. Lynch et al., "Influence of Adjunct Cultures of *Lactobacillus paracasei* ssp. *paracase* or *Lactobacillus plantarum* on Cheddar Cheese Ripening", J. Dairy Science 1999, 82:1618-1628.
Frank V. Kosikowski et al., "Cheese and Fermented Milk Foods", vol. 1, Origins and Principles, Third Edition, 1997.

(Continued)

*Primary Examiner* — Jeffrey P Mornhinweg
(74) *Attorney, Agent, or Firm* — Foley & Lardner LLP

(57) ABSTRACT

The present invention relates to a method for making cheese of the continental type or the cheddar type, especially reduced-fat or low-fat cheese.

20 Claims, No Drawings

(56) References Cited

OTHER PUBLICATIONS

"Sensory analysis—Methodology—Triangle Test", International Standard ISO 4120:2004, pp. 1-15.
"Sensory analysis—Methodology—General guidance for establishing a sensory profile", International Standard ISO 13299: 13299, pp. 1-24.
Sensory analysis—Vocabulary—International Standard ISO 5492:1992 pp. 1-23.
Pieter Walstra et al., "Dariy Science and Technology" Second Edition Taylor and & Francis Group, 2006.

* cited by examiner

METHOD FOR MAKING CHEESE

FIELD OF INVENTION

The present invention relates to a method for making cheese of the continental type or the cheddar type, especially reduced-fat or low-fat cheese.

BACKGROUND OF INVENTION

Continental cheese and Cheddar cheese are traditionally produced by adding a mesophilic starter culture, e.g. comprising lactic acid bacteria of the species *Lactococcus lactis* subsp. *lactis, Lactococcus lactis* subsp. *cremoris, Lactococcus lactis* subsp. *lactis* biovar. diacetylactis, *Leuconostoc mesenteroides* subsp. *cremoris*, to milk. Typically, a coagulant is added after or together with the starter culture.

In the manufacturing of fermented milk products there is a constant need for alternative and improved manufacturing methods. Such desired methods typically aim at improving the manufacturing process e.g. by reducing cost, increasing speed of the overall process and/or improve characteristics of the final product. Desired product improvements include all known product quality parameters such as taste, texture, flavor etc. In fermented milk products the manufacturing process includes the addition of a starter culture performing the specific fermentation. In cheese production, the objective of the starter culture is primarily to acidify the raw material, milk. Often, it is not possible to optimize the performance of the primary starter in a way that secures optimal taste/flavor of the final product.

In the case of cheese production a ripening step is often included in the production process. During the ripening phase proteolysis and lipolysis are key factors for texture and flavor development in the cheese product. In some cheese types ripening cultures such as yeasts, moulds or coryneform bacteria are used. In other cheese types these ripening cultures are not used but still the ripening phase should result in the development of the wanted organoleptic properties of the cheese in a short time frame.

As a result it has been suggested to apply "adjunct cultures" in the manufacturing of fermented milk products aiming at improving the secondary characteristics of the product such as texture and/or flavor. This is of special relevance for reduced-fat or low-fat cheeses.

Cheese varieties can be classified according to the manufacturing process or according to the cheese composition.

Traditionally, cheeses of the continental type are made with mesophile starter cultures. An example of a rather traditional Edam make is given below. Traditional Edam is made according to the following steps (according to: Walstra et al, 2006 Dairy Science and Technology, Second edition, Taylor & Francis, page 703): Milk is standardized in fat content (e.g. 2.5% fat), pasteurized (20 sec/72° C.) and filled into the cheese vat with a temperature of 30° C. KNO3 and CaCl2 might be added to the milk. Milk is afterwards inoculated with the mesophile starter culture. Rennet is added and the coagulation process is taking place during 35 min at 30° C. The coagulum is cut (15 min) and one third of the whey is drained off. Hot water is added and the scalding is made at 33° C. The stir out phase takes 40 min and afterwards the whey is drained off and the curd is transferred into moulds. The curd is pressed in the moulds for 5 h at 1 bar. After a subsequent resting phase of 12 h, the cheeses are salted in a brine (3.5 days).

Cheddar type cheeses are made in a different way, in that they are salted in the curd stage. An example of a rather traditional Cheddar make is given below to illustrate the manufacturing process (according to Walstra et al, 2006 Dairy Science and Technology/Second edition, Taylor & Francis, page 713): Milk is pasteurized (15 sec/71° C.), filled into the cheese vat with a temperature of 30° C. and pre-acidified with addition of starter culture during 40 min at 30° C. Rennet is added and the coagulation process is taking place during 35 min at 30° C. The coagulum is cut (10 min) and during 30 min of stirring the curd/whey is heated up to a scalding temperature of 40° C. The scalding temperature is hold for 60 further minutes. Then the curd settles, fuses into a compact mass and whey is taken off (30 min). Afterwards the cheddaring takes place (100 min) where the curd mass is cut into large strips that are piled up and turned. Prior to salting, the curd is milled into small strips. Salt is added and mixed with the curd strips. The salted curd is then filled into moulds and pressed (16 h/2 bars). After a certain drying phase cheeses are waxed or packed and ripened at relatively low temperature as 8° C.

Cheeses of Emmental type using thermophile starter cultures exclusively in combination with propionic acid bacteria as ripening cultures are not included in the group of continental type cheeses. The addition of propionic acid bacteria in combination with a ripening period at higher temperatures ("warm" ripening phase) leads to hole formation in the cheese by gas production from lactate. Cheeses of the Emmental type are characterized by:
  Fat in Dry matter: 40-55%
  Water content: <40%
  Water in Fat free cheese matter: <55%
  Addition of *Propionibacterium freudenreichii* subsp. *shermani*
  Heating the curd to a temperature above 50° C.
  Warm ripening phase at approximate 20° C. (17-24° C.) during ripening
  Hole formation by gas production of propionic acid bacteria from lactate

SUMMARY OF INVENTION

It has surprisingly turned out that it is possible to improve the texture and/or taste of cheeses of the continental type and the cheddar type by using specific thermophilic *Lactobacillus* strains so far not used as adjunct cultures in these cheese types. The present inventors have found out that adding bacterial strains belonging to species *Lactobacillus delbruecki* subspecies *lactis* (especially a strain with protein degrading activity) to the cheese milk in combination with a traditional starter culture, results in cheeses having an improved texture and/or taste.

In accordance with the surprising finding, the present invention relates to a process for producing cheese of the continental type or the cheddar type (including low or reduced fat cheeses), which comprises adding a *Lactobacillus delbrueckii* subspecies *lactis* strain (especially a strain with protein degrading activity) as adjunct culture to the milk. The invention further relates to the resulting cheese.

DETAILED DISCLOSURE

One aspect of the present invention relates to a process for producing cheese (including reduced fat and low fat cheese), which comprises: adding to milk
  a starter culture, such as culture comprising a strain belonging to a genus selected from the group consisting of: *Lactococcus, Lactobacillus, Leuconostoc, Pediococcus, Streptococcus*, and *Enterococcus*, and a *Lactobacillus delbrueckii* subspecies *lactis* strain; and
a coagulant, such as a milk-clotting enzyme;
heating the mixture to a temperature (or maintaining the temperature) in the range of 20 to 45 degrees C., such as in the range 20 to 43 degrees C. or in the range 25 to 40 degrees C.

In other words, the invention relates to a process for producing cheese comprises adding a starter culture; an adjunct culture; and a coagulant to milk; and heating the mixture to a temperature (or maintaining the temperature) in the range of 20 to 45 degrees C., such as in the range 20 to 43 degrees C. or in the range 25 to 40 degrees C., characterized in that the adjunct culture comprises a *Lactobacillus delbrueckii* subspecies *lactis* strain. It should be understood that the term "mixture" refers to the curd and whey mixture, either in unprocessed or processed form, e.g. some of the whey has been drained from the curd, or some of the whey has been replaced with hot water. Thus the term includes curd that has been separated from some or all of the whey.

In an embodiment, the invention relates to a process for improving the texture and/or taste of cheese, comprising adding to milk
 a starter culture, such as culture comprising a strain belonging to a genus selected from the group consisting of: *Lactococcus, Lactobacillus, Leuconostoc, Pediococcus, Streptococcus*, and *Enterococcus*; and
 a *Lactobacillus delbrueckii* subspecies *lactis* strain; and
 a coagulant;
heating the mixture to a temperature (or maintaining the temperature) in the range of 20 to 45 degrees C., such as in the range 20 to 43 degrees C. or in the range 25 to 40 degrees C.

Other interesting temperature ranges are, in degrees C.: 30-45; 35-45; 35-40; and 37-43. It is presently preferred that the temperature is kept in the specified range for at least 5 minutes (such as for at least 15 minutes, at least 30 minutes or at least 45 minutes), and/or at most 10 hours (such as at most 6 hours, at most 4 hours or at most 2 hours). It should be avoided that the temperature exceeds the upper limit of the range (e.g. 45 degrees C.) for a substantial period of time, such as for more than 30 minutes or more than 1 hour. It is understood that such modifications of the temperature are within the scope of the present invention.

In a preferred embodiment of the process, the (culture of a)*Lactobacillus delbrueckii* subspecies *lactis* strain has an alpha-s1 casein degrading activity degrading activity, such as a high alpha-s1 casein degrading activity, e.g. being able of degrading at least 25% (such at least 40%, at least 50%, at least 55%, at least 60% or at least 70%) of the alpha S1 casein, e.g. assessed in the assay "Assay for assessment of Proteolytic activity/Degradation of alpha s1-casein" (cf. the experimental part below).

It is presently preferred that the (culture of a) *Lactobacillus delbrueckii* subspecies *lactis* strain is able to degrade galactose, e.g. as assessed by the method API 50 CH, bioMérieux, Inc.

The starter culture may be added in an amount of at least 10e4 cell forming units (CFU or cfu) (such as at least 10e5, at least 10e6 or 10e7) per ml milk, and/or the *Lactobacillus delbrueckii* subspecies *lactis* strain is added in amount of at least 10e4 (such as at least 10e5, at least 10e6 or 10e7) CFU per ml milk. In an interesting embodiment, the adjunct strain is added in an amount that results in that at least 25% (such as at least 35%, 50% or even 70%) of the milks alpha-s1 casein is degraded, e.g. measured in the obtained cheese.

It is not critical to the invention which starter culture is used in the process; examples on appropriate cultures are strains of the species: *Lactococcus lactis, Leuconostoc mesenteroides, Pediococcus pentosaceus, Lactobacillus casei, Lactobacillus paracasei, Streptococcus thermophilus, Enterococcus faecium, Lactobacillus helveticus, Lactobacillus delbrueckii* subsp. *bulgaricus* and *Lactobacillus acidophilus*. In an embodiment of the process of the invention the starter culture is a strain of *Lactococcus lactis* subsp. *cremoris*, or *Lactococcus lactis* subsp. *lactis* biovar. diacetylactis.

The process of the invention can be used for making continental type cheese (e.g. gouda, danbo, massdamer, havarti etc), or a cheddar type cheese, including low-fat cheese.

It is presently preferred that no bacteria belonging the genus *Propionibacterium* are added to the milk, especially in a concentration above 10e2 CFU per ml, but the invention relates to processes wherein further bacterial strains are added, such as propione acid bacteria and citric acid bacteria. A further substance may be added during the process of the invention, such as a spice, a color, an antibiotic, or a microorganism.

An embodiment of the invention includes the further step of pressing the mixture obtained in the heating step, either before or after salting. The pressed and salted cheese is normally stored at a temperature in the range of 1 to 20 degrees C., and the aim is that the temperature of the pressed and salted cheese does not exceed 20 degrees C. for a substantial period of time, such as for more than 2 hours, during the process.

A further aspect of the present invention relates to a bacterial strain belonging to *Lactobacillus delbrueckii* subspecies *lactis* having protein degrading capability, such as a (high) alpha-s1 casein degrading activity, e.g. being able of degrading at least 25% (such at least 40%, at least 50%, at least 55%, at least 60% or at least 70%) of the alpha S1 casein in the assay "Assay for assessment of Proteolytic activity/Degradation of alpha s1-casein" (see the experimental part of the present specification). A preferred group is strains, which also are able to degrade galactose, e.g. as assessed by the method API 50 CH, bioMérieux, Inc. Preferred strains are e.g. strains belonging to the group consisting of: strain A (DSM 18885), strain B (DSM 19279) and strain C (DSM 19278), and mutants or variants of these strains which have a (high) alpha-s1 casein degrading activity, e.g. being able of degrading at least 25% (such as at least 40%, at least 50%, at least 55%, at least 60% or at least 70%) of the alpha S1 casein in the assay "Assay for assessment of Proteolytic activity/Degradation of alpha s1-casein".

A still further aspect of the present invention relates to the use of a bacterial strain belonging to *Lactobacillus delbrueckii* subspecies *lactis*, preferably having (high) alpha s1-casein degrading capability (e.g. a strain of the invention), for making cheese of the continental type or cheddar type cheese, including reduced or low fat cheese, especially for increasing the texture and/or taste of the cheese. Optionally the strain has a high protein degrading capability and a galactose degrading capability, for improving the taste and/or flavor of cheese of the continental type or cheddar type cheese.

The last aspect of the present invention relates to cheese which is obtainable by the process of the invention, e.g. a cheese of continental or cheddar type which is produced using a strain of the present invention as adjunct culture. In a preferred embodiment the obtained cheese has improved texture; flavor; and/or taste.

Definitions

By the term "milk" is understood a composition comprising milk from an animal species belonging to the subfamily Bovinae (which includes the domestic cow (Bos taurus) and buffalo) or milk from an animal species belonging to the subfamily Caprinae (which includes goat and sheep). Optionally the milk is acidified, e.g. by addition of an acid (such as citric, acetic or lactic acid) or by addition of an acid producing microorganism. The milk may be raw or processed, e.g. by filtering, sterilizing, pasteurizing, homogenizing etc, or it may be reconstituted dried milk. An important example of "milk" according to the present invention is pasteurized cow's milk. It is understood that the milk may be acidified, mixed or processed before, during and/or after the adding of bacterial cultures.

The term "coagulant" refers to any kind of milk clotting agent, such as a native enzyme derived from microbial or animal tissue sources or a milk clotting enzyme provided as a gene product of recombinant cells expressing a milk clotting enzyme of animal or microbial origin. The term includes bovine chymosin purified from abomasum tissue or made by fermentation (e.g. CHY-MAX™).

In the present context, the term "(high) protein degrading capability" refers to the potential of cultures to degrade alpha s1 casein, especially bovine casein.

In the present context, the term "cheese" includes a product prepared by contacting optionally acidified milk (e.g. by means of a lactic acid bacterial culture) with a coagulant, and draining the resultant curd. Cheeses and their preparation are described in e.g. Cheese and Fermented Milk Foods, by Frank V. Kosikowski.

The term "cheese of the continental type" should be understood as cheeses of the types, Gouda, Danbo, Edam, St. Paulin, Raclette, Fontal etc. and/or cheeses made by a process which includes heating the curd to a temperature that does not exceed 45 degrees C.

In the present context, cheese of the continental type is characterized by:
 Fat in Dry matter: 20-60%
 Water content: 35-57%
 Water in Fat free cheese matter: 53-63%
 Salt content: 1-3.5%
 Pressing step during cheese manufacture process
 Salting after pressing most often in a brine The term "cheese of the cheddar type" should be understood as cheeses of the types as Cheddar, Territorials, American Cheddar, Monterey Jack and Colby, and/or cheeses made by a process which includes heating the salted curd to a temperature that does not exceed 45 degrees C. In the present context, cheese of the cheddar type is characterized by:
 Fat in Dry matter: 20-60%
 Humidity: 34-42%
 Salt content: 1.5-2.5%
 Cheddaring and subsequent Milling step
 Salting after milling but before pressing
 Pressing step The term "reduced fat cheese" refers to cheese having a fat content in the range of 32% to 25% in dry matter, and the term "low fat cheese" refers to cheese having a fat content of less than 25% in dry matter. The person skilled in the art is familiar with the adjustment of the milk fat content in respect to varying protein content of the milk. Fat content is cheese can be determined after van Gulik method ISO 3433, commonly known by the skilled person of the art. Example for Gouda cheese:
full fat cheese: 45% fat in dry matter/ca. 3.1% fat in milk
reduced fat cheese: 30% fat in dry matter/ca. 1.6% fat in milk
low fat cheese: 15% fat in dry matter/ca. 0.7% fat in milk The term "starter culture" relates to any bacterial culture that is suitable for use in milk acidification, such as Bifidobacteria, Brevibacteria, Lactobacilli, Lactococci, Leuconostocs, Micrococci and Pediococci. It will be appreciated that the term starter culture may encompass a culture containing a single strain of bacterium, or more than one bacterial strain. The term may also include genetically modified organisms (GMO's). In any event, the term is well known in the art, and the invention extends equally to all known starter cultures. The term includes bacterial cultures containing a strain of a genus selected from the group consisting of *Lactococcus, Lactobacillus, Micrococcus, Leuconostoc, Pediococcus, Streptococcus, Enterococcus*, etc. such as a strain of a species selected from the group consisting of: *Lactococcus lactis* (incl. *Lactococcus lactis* subsp. *lactis*, *Lactococcus lactis* subsp. *cremoris*, and *Lactococcus lactis* subsp. *lactis* biovar. diacetylactis), *Leuconostoc mesenteroides* (incl subsp. *cremoris*), *Pediococcus pentosaceus*, *Lactobacillus casei* (incl. subsp. *casei*) and *Lactobacillus paracasei* (incl. subsp. *paracasei*), *Streptococcus thermophilus*, *Enterococcus faecium*, *Lactobacillus helveticus*, *Lactobacillus delbrueckii* subsp. *bulgaricus* and *Lactobacillus acidophilus*. Other useful bacterial species are *Bifidobacterium* species including *B. bifidum, B. lactis* and *B. longum, Streptococcus faecium, Leuconostoc lactis, Brevibacterium* species including *B. casei, Staphylococcus* species, *Arthrobacter* species and *Corynebacterium* species.

The term "adjunct culture" refers to a non-starter lactic acid bacteria (NSLAB) that are present during the cheese making. These NSLAB as e.g. *Lactobacillus* strains were shown to contribute to the flavor development (Lynch et al, 1999), and/or microorganisms that are added to the cheese milk to improve development of cheese sensory quality (El-Soda et al, 2000). Adjunct cultures influence the cheese ripening process trough their enzymatic systems involving among others proteinases, peptidases as aminopeptidases, enzymes of the Amino acid catabolism as aminotransferases and esterase. The enzymatic potential is species and strain dependent.

The use of the terms "a" and an and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXPERIMENTAL

Assay for Assessment of Proteolytic Activity/Degradation of Alpha S1-Casein

An Agilent 2000 Bioanalyzer has been used to measure the strains ability to hydrolyse alpha s1-casein.

(i) 400 µl of stock *Lactobacillus lactis* subsp *lactis* culture was added to 200 ml MRS-CM Difco (Batch No. 1318-0403) and incubated at 37° C. until mid-exponential phase growth (OD600=2).

(ii) 30 ml of culture was centrifuged at 4,500 g for 10 min (4° C.) and the cell pellets were washed with 30 ml of ice-cold 50 mM MES buffer, pH 6.5. The cell pellets were re-centrifuged and resuspended in 50 mM MES buffer, pH 6.5, to a final OD600=10.

(iii) 600 µl of cell suspension (OD600=10) was added to 150 µl of bovine alpha$_{s1}$-casein (10 mg/ml in water), and incubated at 30° C. The $\alpha_{s1}$-casein used in these experiments was purified from sodium caseinate as previously described in Rattray et al. (1996). A control reaction, in which the cell suspension was replaced with 600 µl of 50 mM MES buffer, pH 6.5, was also included in the experiment. Samples were withdrawn after 0 and 24 hours' incubation, and the hydrolysis terminated by heating the samples at 90° C. for 10 min. Thereafter, the samples were centrifuged (15,000 g for 5 min, 4° C.), the supernatant withdrawn, and stored at –20° C. until analysis by electrophoresis.

(iv) Electrophoresis was performed using an Agilent 2100 Bioanalyzer and a Protein 50 Assay Kit from Agilent Technologies. Electrophoresis was carried out according to the manufacturer's instructions. Protein 50 Reagents and Supplies (Order No. 5065-4485), Chip Priming Station (Order No. 5065-4401).

The hydrolytic potential of *Lactobacillus lactis* subsp. *lactis* strains was expressed in % of residual alpha$_{s1}$-casein after 24 h in comparison to alpha$_{s1}$-casein at 0 h.

Sensory Analysis

According to International Standards (ISO 5492:1992 Sensory analysis—vocabulary) sensory perception include the attributes "taste", "flavor", "odor" and "aroma". Aroma and odor are primarily associated with the perception by the olfactory organ (nose) prior to and during eating. Taste is defined as the basic tastes perceived by the taste buds in the mouth. Typically, taste is described as "sweet", "sour/acid", "salt" and "bitter". Flavor is defined as a complex combination of the olfactory, gustatory (taste) and trigeminal (feeling) sensations perceived during eating. Typically, flavor is described by words as "pineapple", "diacetyl", "creamy" and "buttery". When food products are to be sensory evaluated it is custom to focus on the perception of taste and flavor.

Thus, when the expression "improved/altered taste and/or flavor" is used herein, it is to be understood as the improved/altered taste and/or flavor as perceived and described by the sensory panel evaluating the cheese of the invention. This should not be taken as an exclusion of possibly altered odor and/or aroma but merely as a simple means to describe the fermented milk product of the invention and distinguish the product from conventional fermented milk products made without the addition of *Lactobacillus delbrueckii* subsp. *lactis* of the invention.

For illustration, in working example 1 herein, one suitable sensory evaluation method is the "Sensory profile". Preferably, the test is performed according to the International Standard (ISO 13299:2003 Sensory analysis—Methodology—General guidance for establishing a sensory profile). This standard describes a guidance on the steps that are common to all sensory profiling. Sensory profiles can be established for products such as e.g. foods and beverages. Sensory profiling is based on the concept that the sensory impression made by the sample consists of a number of identifiable sensory attributes (descriptors), each of which is present to a larger or smaller degree. The list of relevant sensory descriptors, each with its intensity value, is the sensory profile. Sensory profiling can be used to compare a product/sample with a standard or with other similar products, also across all of the senses. Thus, the method is suitable for the present purpose i.e. evaluate the effect of use of an additional ingredient i.e. an adjunct culture in the production of a fermented milk product.

As will be illustrated in the examples herein, the assessors of the sensory panel were able to compare the product made according to the present invention using *Lactobacillus delbrueckii* subsp. *lactis* as adjunct culture and the product made without this adjunct culture. The product made according to the present invention using *Lactobacillus delbrueckii* subsp. *lactis* adjunct culture was recognized as "less bitter", "more soluble", and "less firm".

For illustration, in working example 2 herein, one suitable sensory evaluation method is the "Triangle Test". Preferably, the test is performed according to the International Standard (ISO 4120:2004 Sensory analysis—Methodology—Triangle Test). This standard describes a procedure for determining whether a perceptible sensory difference or similarity exists between samples of two products. The method is a forced-choice procedure and it applies whether a difference can exist in a single sensory attribute or in several attributes. It is appreciated that the method is applicable even when the nature of the difference is unknown (i.e. it determines neither the size nor the direction of difference between samples, nor is there any indication of the attributes responsible for the difference). Furthermore, the method is effective for a) determining that either a perceptible difference results (triangle testing for difference), or a perceptible difference does not result (triangle testing for similarity) when, for example, a change is made in ingredients, processing, packaging, handling or storage. Thus, the method is suitable for the present purpose i.e. evaluate the effect of addition of an additional ingredient i.e. an adjunct culture.

As will be illustrated in the examples herein, the assessors of the sensory panel were able to distinguish the product made according to the process of the invention.

Example 1

Production of Low Fat Continental Type Cheese with *Lactobacillus delbrueckii* Subsp. *Lactis* Adjunct Culture Low-fat cheeses (15% fat in dry matter and 59-60% moisture in non-fat substance) were made from pasteurized (72° C. for 15 s) bovine milk using chymosin (CHY-MAX™ Plus, Chr. Hansen A/S) and a frozen DL-starter culture (0.01% w/w CH-N19 Direct vat set, Chr. Hansen A/S).

Experimental cheeses were made with the starter culture alone or in combination with specific *Lactobacillus delbrueckii* subsp. *lactis* strains respectively. One strain was *Lactobacillus delbrueckii* subsp. *lactis* A (DSM 18885) and the other strain was *Lactobacillus delbrueckii* subsp. *lactis* B (DSM 19279).

Milk with a fat content of 0.7% and protein content of 3.6% was pasteurized (72° C. for 15 sec). Three small scale cheese vats were filled with 170 kg of the milk at 32° C. respectively. While there was a slow agitation of the milk, 0.015% KNO$_3$ (Kirsh Pharma GmbH, Salzgitter, Germany) was added. As starter culture and adjunct culture frozen Direct Vat Set (DVS) cultures were applied. The starter culture F-DVS-CHN-19 (Chr. Hansen A/S) was inoculated at 0.01% w/w in all three vats. One vat was simultaneously inoculated with the strain *Lactobacillus delbrueckii* subsp.

*lactis* A (DSM 18885) and another vat was simultaneously inoculated with the strain *Lactobacillus delbrueckii* subsp. *lactis* B (DSM 19279). The inoculation level of the *Lactobacillus delbrueckii* subsp. *lactis* strains was $10^6$ cfu/ml vat milk.

After 35 minutes of milk ripening, rennet of the type CHY-MAX™ Plus (Chr. Hansen A/S, Hørsholm, Denmark) was added and the milk coagulated for 45 min.

The coagulum was cut in small squares (5×5 mm) and pre-stirred at a slow speed for 25 minutes. Then the first portion of whey (20%) was drained off. The agitation was enhanced and after 5 minutes warm scalding water was added during 10 minutes. The temperature was thereby raised to 35° C. After scalding, 15 kg of cold water were added and the agitation continued for 15 minutes, resulting is a total stirring time of 55 minutes.

Then the curd was pre-pressed under the whey for 10 minutes at 1 bar and 15 minutes at 2.5 bar. Afterwards the whey was drained off and the pre-pressed cheese was cut in two pieces and placed in perforated moulds (30×30 cm). The cheeses were then pressed for 15 min at 2 bar, 50 minutes at 3.5 bar and 50 minutes at 5 bar.

After this the cheese were placed in cold (12° C.) tap water to cool down for 17 hours. After 14 hours in the brine the cheeses were placed on perforated plates to dry of for 35 hours at 9° C. The cheeses were vacuum-packed in Cryovac® BL1 L plastic bags (Cryovac, St. Neots, Belgium) and placed in hard plastic boxes.

The cheeses were ripened for 9 weeks. They were first stored at 9° C. for 1 week, then 13° C. for 3 weeks and finally 9° C. for 5 weeks. The cheeses were turned around once every 7 days over the first four weeks of ripening.

Sensory Evaluation

An expert panel evaluated the cheeses organoleptically after 9 weeks of ripening. A randomized three-digit identification code was given to each of the samples. The trays with cheese samples were tempered in a thermostatic cupboard at 12° C. before the sensory evaluation. The panelists were asked to rate each cheese on a 15 cm undifferentiated scale for each sensory attribute (0 being low intensity and 15 being high intensity). The flavor profiles of each cheese were described independently by five expert panelists, and after the assessment the results were evaluated leading to a consensus profile of each cheese.

| Sensory descriptor | Control cheese (no adjunct culture) | Cheese made with adjunct culture *Lactobacillus delbrueckii* subsp. *lactis* A (DSM 18885) | Cheese made with adjunct culture *Lactobacillus delbrueckii* subsp. *lactis* B (DSM 19279) |
|---|---|---|---|
| Firmness | 7.5 | 4.8 | 5.5 |
| Solubility | 7.5 | 9.4 | 8.9 |
| Bitterness | 7.5 | 5.8 | 6.4 |

The firmness of the cheese made with adjunct culture *Lactobacillus delbrueckii* subsp. *lactis* A and B was reduced and the solubility was enhanced in comparison to the control cheese. The addition of the adjunct cultures *Lactobacillus delbrueckii* subsp. *lactis* A and B led to a reduction of bitterness in comparison to the control cheese without adjunct culture.

Example 2

Production of Cheddar Cheese with *Lactobacillus delbrueckii* Subsp. *Lactis* Adjunct Culture Full-fat Cheddar cheeses (50% fat in dry matter and 51-52% moisture in non-fat substance), were made from pasteurized (72° C. for 15 s) bovine milk using chymosin (CHY-MAX Plus, Chr. Hansen A/S) and a frozen RST-starter culture (0.008% w/w RST630 Direct vat set, Chr. Hansen A/S). Experimental cheeses were made with the starter culture alone or in combination with specific *Lactobacillus delbrueckii* subsp. *lactis* strains respectively. One strain was *Lactobacillus delbrueckii* subsp. *lactis* A (DSM 18885) and the other strain was *Lactobacillus delbrueckii* subsp. *lactis* B (DSM 19279).

Milk with a fat content of 3.7% and protein content of 3.4% was pasteurized (72° C. for 15 sec). Three small scale cheese vats were filled with 150 kg of the milk at 32° C. respectively. As starter culture and adjunct culture frozen Direct Vat Set (DVS) cultures were applied. The starter culture F-DVS-RST630 (Chr. Hansen A/S) was inoculated at 0.008% w/w in all three vats. One vat was simultaneously inoculated with the strain *Lactobacillus delbrueckii* subsp. *lactis* A (DSM 18885) and another vat was simultaneously inoculated with the strain *Lactobacillus delbrueckii* subsp. *lactis* B (DSM 19279). The inoculation level of the *Lactobacillus delbrueckii* subsp. *lactis* strains was $10^6$ cfu/ml vat milk. After 45 minutes of milk ripening, 27 g of rennet of the type CHY-MAX™ Plus (Chr. Hansen A/S, Hørsholm, Denmark) was added and the milk coagulated for 45 min.

The coagulum was cut in small squares (5×5 mm) and pre-stirred at a slow speed for 15 minutes. Then the agitation was enhanced and the warming up to scalding temperature of 40° C. was done in 40 minutes. The cured was stirred at 40° C. for 20 minutes.

Then the way was removed, and the curd sedimented to the bottom of the vats. After 20 minutes, the curd was cut into 6 slices. The slices were turned 5 times during 90 minutes, piling them up higher and higher at each turning step. Then the curd was milled and salted on a table with 4% NaCl. After 10 minutes, the curd of one vat was filled in one mould (approximate 16 kg) and pre-pressed for 15 min at 2 bars. Then the pressing was carried out at 7 bars for 17 h.

After pressing the cheeses were removed from the moulds and vacuum packed in Cryovac® BL1 L plastic bags (Cryovac, St. Neots, Belgium) and stored at 9° C. for a defined storage time.

Sensory Evaluation

Sensory analysis was done by triangular test with 12 assessors after 17 weeks of storage.

| Test | Cheeses evaluated in triangular test | | Significant difference between control and test cheese perceived | Number of correct answers |
|---|---|---|---|---|
| 1 | RST630 (control cheese) | RST630 + *Lactobacillus delbrueckii* subsp. *lactis* A (DSM 18885) | yes | 10 |
| 2 | RST630 (control cheese) | RST630 + *Lactobacillus delbrueckii* subsp. *lactis* B (DSM 19279) | yes | 10 |

The test cheeses made with the adjunct cultures were assessed to be softer and stickier.

*Lactobacillus delbrueckii* subsp. *lactis* strain A was deposited 19 Dec. 2006 at Deutsche Sammlung von Mikroorganismen and Zellkulturen GmbH (DSM) and given the accession number DSM 18885. *Lactobacillus delbrueckii* subsp. *lactis* strains B and C were deposited 12 Apr. 25, 2007 at DSM and given the accession numbers DSM 19279 and DSM 19278, respectively. All deposits were made according to the Budapest treaty on the international recognition of the deposit of microorganisms for the purposes of patent procedure.

For all deposited microbial organisms mentioned in the present patent application the following applies.

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

Walstra et al, 2006 Dairy Science and Technology/Second edition, Taylor & Francis Cheese and Fermented Milk Foods, by Frank V. Kosikowski.
Lynch et al, 1999. Influence of *Lactobacillus paracasei* ssp. *paracasei* or *Lactobacillus plantarum* on Cheddar cheese ripening. Journal of Dairy Science. Vol. 82 Issue. 8: 1618-1628.
El-Soda et al, 2000. Adjunct cultures: Recent Developments and Potential Significance to the Cheese Industry. Journal of Dairy Science. 83: 609-619.
International Standards ISO 5492:1992, ISO 41 20:2004 and ISO 13299:2003.
Rattray et al, 1996. Specificity of an extracellular proteinase from Brevibacterium linens ATCC 9174 on bovine alpha s1-casein. Appl. Environ. Microbiol. 62:501-506.

All references cited in this patent document are hereby incorporated herein in their entirety by reference.

The invention claimed is:

1. A process for producing Cheddar cheese, comprising:
   adding to milk
   a starter culture;
   an adjunct culture comprising a *Lactobacillus delbrueckii* subspecies *lactis* strain selected from the strain deposited at Deutsche Sammlung von Mikroorganismen und Zellkulturen GmbH (DSMZ) under accession number DSM 18885 and the strain deposited at DSMZ under accession number DSM 19279; and
   a coagulant; and
   heating the mixture to a temperature in the range of from 20 to 45° C.

2. A process for improving the texture and/or taste of Cheddar cheese, comprising adding to milk
   a starter culture;
   an adjunct culture comprising a *Lactobacillus delbrueckii* subspecies *lactis* strain selected from the strain deposited at DSMZ under accession number DSM 18885 and the strain deposited at DSMZ under accession number DSM 19279; and
   a coagulant; and
   heating the mixture to a temperature in the range of from 20 to 45° C.,
   wherein the Cheddar cheese has an improved texture and/or taste as compared to a Cheddar cheese made by a comparable process without said adjunct culture.

3. The process according to claim 1, wherein the starter culture is added in an amount of at least $10^4$ CFU per ml milk, and/or the adjunct culture comprising the *Lactobacillus delbrueckii* subspecies *lactis* strain is added in an amount of at least $10^4$ CFU per ml milk.

4. The process according to claim 1, wherein the temperature is kept within the specified range for a period of 10 minutes to 4 hours, followed by one or more steps selected from the group consisting of draining the whey from curd, cutting the curd, and pressing the curd.

5. The process according to claim 1, wherein bacteria belonging to the genus *Propionibacterium* are added to the milk in a concentration below $10^2$ CFU per ml.

6. The process according to claim 1, further comprising pressing the mixture obtained in the heating step, either before or after salting, to obtain pressed and salted cheese.

7. A Cheddar cheese obtained by the process of claim 1.

8. The process according to claim 1, wherein no bacteria belonging to the genus *Propionibacterium* are added to the milk.

9. The process of claim 1, wherein the mixture is heated to a temperature in the range of from 20 to 43° C.

10. A Cheddar cheese obtained by the process of claim 2.

11. The process of claim 2, wherein the mixture is heated to a temperature in the range of from 20 to 43° C.

12. The process according to claim 6, further comprising storing the pressed and salted cheese at a temperature in the range of from 1 to 20° C.

13. The process according to claim 1, wherein the adjunct culture comprises strain DSM 18885.

14. The process according to claim 1, wherein the adjunct culture comprises strain DSM 19279.

15. The process according to claim 2, wherein the adjunct culture comprises strain DSM 18885.

16. The process according to claim 2, wherein the adjunct culture comprises strain DSM 19279.

17. The Cheddar cheese according to claim 7, wherein the adjunct culture comprises strain DSM 18885.

18. The Cheddar cheese according to claim 7, wherein the adjunct culture comprises strain DSM 19279.

19. The Cheddar cheese according to claim 10, wherein the adjunct culture comprises strain DSM 18885.

20. The Cheddar cheese according to claim 10, wherein the adjunct culture comprises strain DSM 19279.

* * * * *